(12) United States Patent
Leuenberger Jockel (10) Patent No.: US 9,285,324 B2
(45) Date of Patent: Mar. 15, 2016

(54) SENSOR FOR USE IN A LIQUID MEDICATION DELIVERY SYSTEM

(71) Applicant: Roche Diagnostics International AG, Rotkreuz (CH)

(72) Inventor: James Leuenberger Jockel, Liestal (CH)

(73) Assignee: Roche Diabetes Care, Inc., Indianapolis, IN (US)

(*) Notice: Subject to any disclaimer, the term of this patent is extended or adjusted under 35 U.S.C. 154(b) by 388 days.

(21) Appl. No.: 13/721,333

(22) Filed: Dec. 20, 2012

(65) Prior Publication Data

US 2013/0107267 A1    May 2, 2013

Related U.S. Application Data

(63) Continuation of application No. PCT/EP2011/058715, filed on May 27, 2011.

(30) Foreign Application Priority Data

Jun. 28, 2010   (EP) .................................. 10167585

(51) Int. Cl.
| | | |
|---|---|---|
| *G01N 21/85* | (2006.01) | |
| *G01N 21/55* | (2014.01) | |
| *A61M 5/142* | (2006.01) | |
| *A61M 5/168* | (2006.01) | |
| *A61M 5/14* | (2006.01) | |
| *A61M 5/36* | (2006.01) | |

(52) U.S. Cl.
CPC .......... *G01N 21/85* (2013.01); *A61M 5/14244* (2013.01); *A61M 5/16831* (2013.01); *A61M 5/16854* (2013.01); *G01N 21/55* (2013.01); *A61M 5/141* (2013.01); *A61M 5/36* (2013.01); *A61M 2005/14268* (2013.01); *A61M 2005/16868* (2013.01); *A61M 2205/3306* (2013.01); *A61M 2205/3313* (2013.01)

(58) Field of Classification Search
None
See application file for complete search history.

(56) References Cited

U.S. PATENT DOCUMENTS

| | | | |
|---|---|---|---|
| 4,238,207 A | 12/1980 | Ruschke | |
| 4,554,837 A | 11/1985 | Danby et al. | |
| 6,936,035 B2* | 8/2005 | Rake et al. | 604/246 |
| 7,914,482 B2* | 3/2011 | Urich et al. | 604/65 |
| 8,081,069 B2 | 12/2011 | Haueter et al. | |
| 8,308,688 B2* | 11/2012 | Valle et al. | 604/151 |
| 2008/0294094 A1 | 11/2008 | Mhatre et al. | |
| 2009/0165876 A1* | 7/2009 | Atkin et al. | 137/825 |

FOREIGN PATENT DOCUMENTS

| | | |
|---|---|---|
| EP | 1818664 A1 | 8/2007 |
| EP | 2022519 A1 | 2/2009 |

OTHER PUBLICATIONS

Kohl, M.J., et al., "A microfluidic experimental platform with intenal pressure measurements", Sensors and Actuators, A 118, pp. 212-221 (2005).

* cited by examiner

*Primary Examiner* — Michael A Lyons
*Assistant Examiner* — Amanda Merlino
(74) *Attorney, Agent, or Firm* — Roche Diabetes Care, Inc.

(57) ABSTRACT

A sensor for use in a liquid medication delivery system is presented. The sensor has a micro-fluidic chamber comprising a rigid bottom structure, a cover, and an optical detection system that emits one or more light beams toward the cover membrane and to observe the one or more light beams reflected from the cover membrane. The optical detection system is on a side of the bottom structure opposite to the cover membrane.

15 Claims, 8 Drawing Sheets

Fig. 1

Prior Art

SENSOR FOR USE IN A LIQUID MEDICATION DELIVERY SYSTEM

CROSS-REFERENCE TO RELATED APPLICATIONS

This application is a continuation of PCT/EP2011/058715, filed May 27, 2011, which is based on and claims priority to EP 10167585.8, filed Jun. 28, 2010, which is hereby incorporated by reference.

BACKGROUND

The present disclosure generally relates to sensors for use in liquid medication delivery systems and, in particular, to sensors for use in liquid medication delivery systems, with a micro-fluidic chamber and optical detection system, to infusion pump devices and liquid medicament delivery systems with such sensors, and the use of such sensors for measuring the pressure and/or the presence of air bubbles in a fluidic system.

Devices for the automated release of liquid medications are generally used with patients who have a continuous, and in the course of the day varying, need of a medicine that can be administered by subcutaneous infusion. Specific applications are, for example, certain pain therapies and the treatment of diabetes. In such cases, computer controlled infusion pumps are used, which can be carried by the patient on the body, and which contain a certain amount of liquid medication in a medicine reservoir. The medicine reservoir often comprises medicine sufficient for one or several days. The liquid medication is supplied to the patient from the medicine reservoir through an infusion cannula or an injection needle.

Particularly in self-administration of medications, for example insulin, the patients using the medication in question and administering it themselves by an infusion pump tend to emphasize convenience and discretion. As a consequence, the acceptable dimensions of such infusion pumps are limited in order not be evident through clothing and to be carried as comfortably as possible. In an advantageous type of infusion pump, the liquid medication is obtained by a downstream pump from a flexible container. Flexible containers have the advantage of a smaller volume surplus of the container in relation to its content, which reduces the manufacturing costs and enables design of infusion pumps of smaller overall dimensions.

In the context of liquid medication administration via an infusion pump, sensors can be used for controlling the dosing, monitoring the correct operation of the system, and for fast detection of faults and hazards, such as occluded infusion lines or cannulas, empty containers, or malfunctioning pump systems. A pressure sensor is typically arranged in the fluid path downstream of a pump and upstream of an infusion cannula.

Such pressure sensors typically comprise a micro-fluidic chamber filled with liquid and fluidly connected to the fluidic system. The micro-fluidic chamber is covered by a flexible, resilient membrane, such that a pressure difference between the fluidic pressure inside the sensor chamber and the outside (such as atmospheric) pressure will temporarily deform the membrane. The resulting deflection of the membrane can then be measured in order to determine the internal pressure of the fluidic system.

Figure 1:
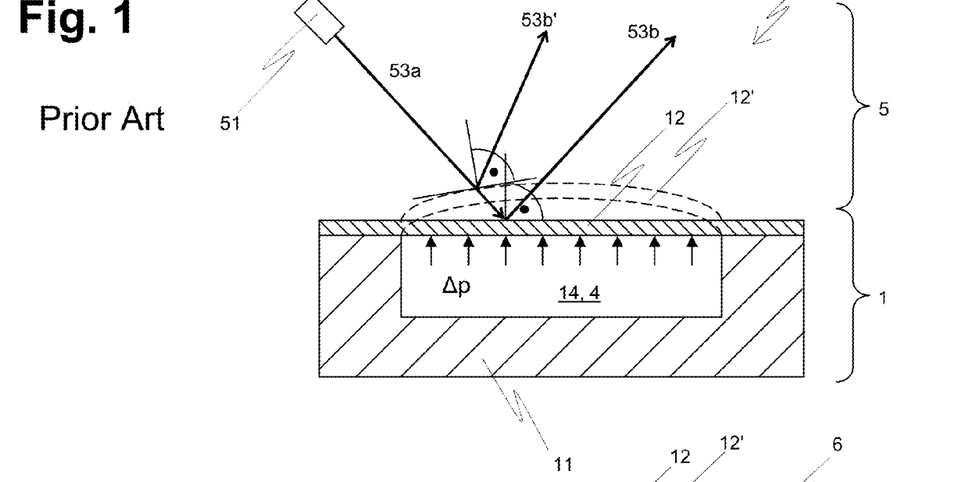
FIG. 1 illustrates a sensor in a cross-sectional view, with a micro-fluidic chamber and an optical detection system according to the prior art.

A suitable approach to measure the deformation of the membrane is optical detection of a light beam reflected off of the membrane. FIG. 1 schematically shows such a pressure sensor 6 according to the prior art. A micro-fluidic chamber 1 that is connected to a fluidic system comprises a rigid bottom substrate 11 and a flexible, resilient top cover 12, for example, a membrane. An optical detection system 5 is arranged to measure a deformation of the cover membrane 12 by determining the interaction of a light beam 53a with the cover membrane 12. For that purpose a light emitting device 51, e.g. a laser diode, directs a light beam 53a at a certain angle onto the surface of the cover membrane 12, where it is reflected 53b. The pressure difference Δp between the inner volume 14 of the micro-fluidic chamber 1 and the outer environment acts on the cover membrane 12, and deforms it to a certain extent 12', depending on the pressure difference. As a result the angle of the reflected light beam changes and the beam 53a is transversely shifted. By observing the position of the reflected light beam 53b, 53b', the deformation of the cover membrane 12 can be measured, and based on the obtained results a pressure difference value can be determined.

To observe the reflected light beam, a detector in an optical detection system 5 must be designed to be movable, or a multiplicity of detectors at different positions and at different angles must be included in a device according to the prior art. Both of these aspects make such sensor devices expensive and difficult to make.

The flexible, resilient top cover membrane 12 is rather delicate and thus prone to damage. A compromised or even damaged cover membrane would lead to erroneous pressure measurements and/or to leaking of the fluidic system, both of which are not acceptable. Consequently the top cover membrane 12 should be protected from mechanical damage as well as other detrimental environmental influences. At the same time the flexible top cover 12 has to remain accessible to the optical detection system 5.

The optical detection system 5 can be arranged within a suitable protective cover for the membrane 12. However, since a fluidic system of a liquid infusion pump system including any pressure sensor is generally designed as a disposable part, for hygienic reasons, such a solution is very expensive, since any light emitting and receiving devices of the detector system 5 would have to be discarded together with the micro-fluidic chamber 1.

It is important that the micro-fluidic chamber 1 of the pressure sensor device is free of air bubbles, in order to avoid systematic or random measurement errors. Air bubbles in the micro-fluidic sensor chamber (and more generally, anywhere within a fluidic system) reduce the stiffness of the fluidic system, and thus delay the response of the sensor to pressure changes that may occur if the fluidic system becomes occluded. The resulting irreproducible measurement errors can reduce the dosing accuracy of an infusion pump and increase the response time to an occlusion event.

Air bubbles present in a fluidic system of an infusion pumps, particularly in the pump system, but also in other components such as the container, also cause further problems. If air bubbles remains in the fluidic system, they may be administered instead of the liquid medication, which leads to potentially dangerous dosing errors. Furthermore, the administration of air into a patient should be generally avoided for medical reasons.

A further problem of fluidic systems, particularly in infusion pumps, is the dead volume in the fluidic system. The dead volume cannot be used, meaning that it cannot be emptied or drained completely. Thus, the dead volume considerably increases the effective cost per dose and thus of the overall therapy cost, since a certain percentage of the liquid medication inevitably remains in the fluid system and has to be disposed. This negative cost effect is particularly important for expensive medications. Furthermore, the relative portion of a certain dead volume of a given overall reservoir size increases with decreasing absolute reservoir size. Minimizing the dead volume therefore becomes more and more important with decreasing reservoir size.

To avoid air bubbles in the micro-fluidic chamber when the fluidic system is filled the first time, the so-called priming of the system, the chamber has to be filled in a controlled manner. However, this goal may be impeded by an uncontrolled orientation of the micro-fluidic chamber in space during this first filling procedure, since the gravitation field leads to buoyancy forces that act on the air bubbles. Depending on the orientation and the design of the micro-fluidic chamber, air bubbles may be caught in certain areas of the chamber.

Due to the many problems that may be caused by air bubbles in a fluidic system, there is a need for reliable sensors for use in infusion pumps for liquid medication, such as a pressure sensor and/or an air bubble sensor, that are able to detect air bubbles in fluidic systems that has small dead volume, inexpensively manufactured, a simpler optical detection system, is insensitive to small variations in the assembly of its components and has sensitive parts protected against mechanical damage.

SUMMARY

According to the present disclosure, a sensor for use in a liquid medication delivery system is presented. The sensor comprises a micro-fluidic chamber having a rigid bottom structure and a cover and an optical detection system that emits one or more light beams toward the cover and that observes the one or more light beams reflected from the cover. The optical detection system is on a side of the bottom substrate opposite to the cover.

Accordingly, it is a feature of the embodiments of the present disclosure to provide reliable sensors for use in infusion pumps for liquid medication, such as a pressure sensor and/or an air bubble sensor, that are able to detect air bubbles in fluidic systems that has small dead volume, inexpensively manufactured, a simpler optical detection system and is insensitive to small variations in the assembly of its components and has sensitive parts protected against mechanical damage. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A sensor for use in a liquid medicament delivery system can have a micro-fluidic chamber comprising a rigid bottom structure and a cover and an optical detection system that emits one or more light beams toward the cover and observes the one or more light beams reflected from the cover. The optical detection system can be on a side of the bottom structure opposite to the cover.

Advantageously, the one or more light beams impinging on the cover and/or the one or more reflected light beams can pass through the bottom structure of the micro-fluidic chamber. A reusable part comprising the optical detection system can be coupled to a disposable part comprising the micro-fluidic chamber.

In one embodiment, the cover can be a flexible, resilient cover membrane and the optical detection system can determine a deformation of the cover membrane. Such a sensor may be used as a pressure sensor device.

When there is no pressure difference between the external pressure and the internal pressure of the fluidic system, the top cover membrane can remain flat. In the case of a positive pressure difference, the membrane can bulge outwards. The resulting displacement of the outer surface of the flexible membrane can then be used to determine the current pressure difference.

The optical detection system can measure the deformation of the cover membrane through the bottom structure and the liquid-filled inner volume of the micro-fluidic chamber. Thus, the outer side of the sensitive membrane can be protected against mechanical damage and environmental influences by placing an inexpensive protective cover over the membrane.

In another embodiment, the wavelength of the emitted light beams can be chosen such that a liquid in the micro-fluidic chamber can show a high absorption coefficient at this wavelength. Such an embodiment can be particularly advantageous as an air bubble sensor. In yet another embodiment, the optical detection system can comprise two or more photo sensors or a photo sensor array. The one or more light beams can be reflected on a fluid-contacting surface of the cover.

The liquid in the fluid system can generally be water or an aqueous solution. For water, advantageous wavelengths can be, for example, about 630 nm or about 1400 nm. An absorption maximum for a typical insulin formulation is given at about 270 nm. Thus such a wavelength can be particularly advantageous for use with insulin pump systems.

When an air bubble passes a light beam, the absorbance along the light path can be considerably reduced, and more light can be detected. Thus such a sensor can be used to identify the presence of air in the path of a light beam, and thus can be able to detect the passage of an air bubble. The meaning of the term "air" can not only include air as such, but any gas or composition of gases that may be present in a fluidic system, particularly pure nitrogen or other protective gases.

If the device comprises two or more photo sensors, or even a photo sensor array, the measured signal on the different detectors can be assessed in relation to the signal on the other detectors, in order to measure of the deflection of a cover membrane, and thus to determine the pressure in the fluidic system. For detecting the presence of air in the light path, on the other hand, and thus the detection of an air bubble, the absolute intensity of the detected light can be assessed. These two channels of information can essentially be independent from each other. In the case where there is only one photo sensor used in a sensor, it can also be possible to detect an air bubble. An air bubble can result in an increase of the detected light signal, while a deflection of the cover membrane can deflect the light beam from the light sensor, thereby decreasing the detected light signal. Consequently, a sensor can have the particular advantage that it can be realized in such a way that it can be used as a pressure sensor and an air bubble sensor at the same time.

In one embodiment, the bottom structure can comprise prism-like structures for coupling a light beam from a bottom structure material into a liquid in an inner volume of the micro-fluidic chamber, and/or from the liquid into the bottom structure material.

One of the advantages of using such prismatic structures can be that the path of the returning reflected light beam can be defined by the prism structures. Optical sensors can be arranged under the prism structures. Thus, the optical detection system can be realized as a static system without moving parts. Only a small, defined number of detectors may be needed, which can be easily aligned in regard to the prism structures.

The correct function of the optical detection system can be insensitive to small variations in the position and orientation of the detectors. Thus the needed accuracy in the manufacturing and assembling process can be decreased, which can reduce the overall cost of the sensor device.

In one embodiment, the top cover membrane can be gas-permeable, which can have the advantage that any air bubble remaining in the sensor can drain through the cover membrane.

In one exemplary embodiment, one or more walls can be positioned in the micro-fluidic chamber, the walls defining a fluid channel therebetween such that the fluid channel can extend from an inlet of the micro-fluidic chamber to an outlet of the micro-fluidic chamber. Each of the walls can have a height less than a height of the micro-fluidic chamber defined by the distance between the bottom structure and the cover membrane, so as to define a fluid gap between a top surface of each wall and the cover membrane. The dimensions of the walls and the micro-fluidic chamber can be chosen such that the fluid gap can be filled with liquid by capillary forces via the fluid channel when liquid is introduced into the fluid channel. In other words, the fluid gap adjacent to a section of the fluid channel filled by a liquid introduced into the micro-fluidic chamber can be filled with the liquid by capillary forces.

Such a sensor can have a considerably reduced dead volume compared to the state of the art. In addition, in the case of a negative pressure difference, where the cover membrane can be displaced inwards toward the chamber, the walls can in certain embodiments support the cover membrane, thereby avoiding an occlusion of the micro-fluidic chamber by the membrane itself.

Prism-like structures can be provided in the walls for coupling a light beam from a bottom structure material of the wall into a liquid in an inner volume of the micro-fluidic chamber and/or from the liquid into the bottom structure material.

Advantageously, at least a part of the surface of the bottom structure, and/or the walls, and/or the top cover membrane facing toward an inner volume of the chamber can be hydrophilic. This can increase the capillary forces in the gap, particularly for aqueous liquids.

In one embodiment, the height of the gap can lie between about 0.02 and about 0.2 mm. In another embodiment, the height of the gap can lie between about 0.05 and about 0.15 mm. The fluid channel can have a curved or meander-like shape, or may be straight. Some embodiments can have two or more fluid channels.

An additional conduit bypassing the micro-fluidic chamber can be provided, by fluidly connecting an inlet conduit and an outlet conduit of the micro-fluidic chamber, which can have the advantage of increasing the flow capacity of the micro-fluidic chamber and thus of the sensor. Advantageously, the width of an inlet of the bypass conduit can be smaller than the width of the inlet conduit, to prevent air bubbles from entering the bypass conduit.

In another embodiment, one or more additional outlets conduits can branch off from the fluid channel.

Since the micro-fluidic chambers can be manufactured in large numbers and on continuous production lines, the effective cost per piece can be sufficiently low that they can be realized as single-use products.

Figure 2:
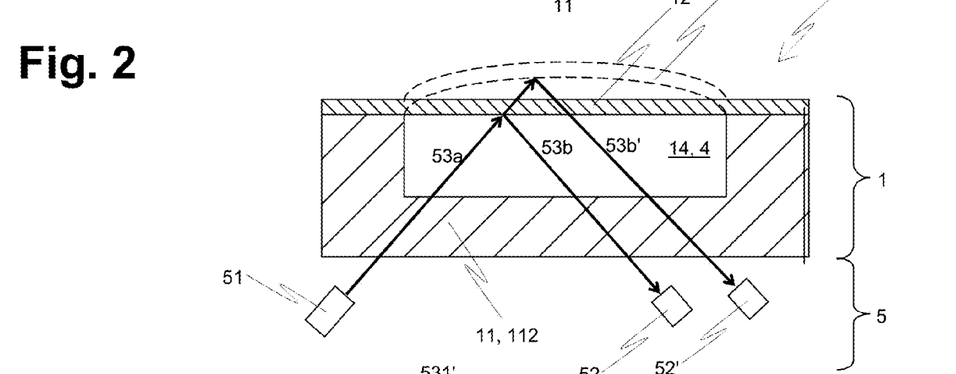
FIG. 2 illustrates a sensor in a cross-sectional view according to an embodiment of the present disclosure.

A first embodiment of a sensor 6 is depicted in FIG. 2, in a cross-section through the micro-fluidic chamber 1 of the sensor 6. The micro-fluidic chamber 1 can comprise a bottom structure 11 and top cover membrane 12, which can define an inner volume 14 of the micro-fluidic chamber 1. The micro-fluidic chamber 1 can be fluidly connected to a fluidic system (not shown). The cover membrane 12 can be flexible and resilient.

During operation of the sensor 6 as a pressure sensor, the inner volume 14 of the micro-fluidic chamber 1 can be filled with liquid. The pressure difference $\Delta p$ between the liquid of the inner volume 14 and the pressure (such as atmospheric pressure) of the outer environment can act on the cover membrane 12 and can bulge the membrane outwards 12'. When the pressure difference drops, the deformed and thus biased membrane 12 can return toward the unloaded, flat state. The amount of deformation of the cover membrane 12 can depend on the pressure difference Δp. Thus the deformation of the membrane 12 can be used to measure the pressure difference.

Using an elastomeric polymer as the material for the cover membrane 12, a circular membrane with a diameter in a range of, for example, about 2 to about 7 mm can be used to measure pressure differences between about 0 and about 200 mbar. For larger pressure differences, smaller diameters can be used, since the deformation of the membrane 12 cannot exceed certain mechanical limits defined by the materials used.

In one embodiment, a light emitting device 51, for example, a laser diode or a light emitting diode, can emit a collimated light beam 53a toward the top cover membrane 12. The path of the light beam 53a can run through the transparent bottom structure 11 of the micro-fluidic chamber 1 and the liquid medium 4 in the inner volume 14. The bottom structure 11 can be advantageously manufactured from a transparent polymer material, such as, for example PMMA or polystyrene.

Upon transition of the light from the bottom structure material 112 to the liquid medium 4, the light beam 53a can be refracted, depending on the ratio of refraction indices of the two materials. The light beam 53a can then be reflected by the inner and/or the outer surface of the cover membrane 12. The cover membrane 12 may be metal vapor coated to increase reflection. The reflected beam 53b can pass again the liquid 4 and the bottom structure material 112, and finally can be received by a photo sensor 52, 52' such as, for example, a photo diode or a photo transistor.

Both the light emitting device 51 and the photo sensors 52, 52' can be located on the side of the micro-fluidic chamber 1 opposite to the cover membrane 12. Therefore, a pressure sensor 6 as shown in FIG. 2 can have the particular advantage over the prior art that the optical detection system 5 may not need to access to the outer surface of the cover membrane 12. Thus, by coupling the light through the bottom structure 11 of the micro-fluidic chamber 1, the cover membrane 12 can have a protective cover or casing (not shown), shielding the cover membrane 12 from mechanical damage and environmental influences. There may be no need for high accuracy of the positioning or the optical characteristics of the protective cover, which can reduce manufacturing costs.

Furthermore, the protective cover can be used to restrict the deformation of the cover membrane 12 to a certain maximum level, thereby preventing the membrane 12 from irreversible damage due to overpressure in the fluidic system. Such an advantageous, additional use of the cover member 12 would not be possible if the membrane 12 would have to be optically accessible from the outside.

The optical detection system 5 can be part of a reusable subunit of the sensor 6, which can be releasably attached to the lower side of the micro-fluidic chamber 1, opposite to the cover membrane 12, which can be permanently and inaccessibly protected by a cover. The micro-fluidic chamber 1 can be part of a disposable subunit of the sensor 6, comprising all parts that come into contact with the liquid medication and cannot be reused. In one embodiment, the optical detection system 5 can be part of a reusable unit of an infusion pump, which can be releasably coupled to a disposable unit of the pump, including the fluidic system with the micro-fluidic chamber 1.

When the cover membrane 12 is deformed 12', the path of the reflected light beam can be shifted and deflected 53b', depending on the degree of deformation. A photo sensor 52 can only receive the light beam 53b as long as it is in a certain spatial range. Thus in a setup of a sensor 6 with one single photo sensor, can be only possible to determine if the deformation of the cover membrane 12, or the corresponding pressure differential, lies in a predefined target range, corresponding to the spatial detection range of the photo sensor 52. In such an embodiment, the optical detection system 5 thus can deliver a binary on/off signal correlated to a certain pressure threshold, which can be used by a control unit of an infusion pump system. Such a relatively simple system can be completely sufficient to detect an occlusion in a fluid line.

In the embodiment shown in FIG. 2, two photo sensors 52, 52' can be provided. A first sensor 52 can receive the reflected light beam 53b over a first range of membrane deformations, including the state with undeformed membrane 12, equivalent to zero pressure difference. A second photo sensor 52' can receive the reflected light beam 53b' over an adjacent range of deformation, including a maximum allowable deformation state of the membrane 12'.

Instead of one or two photo sensors, a multitude of sensors may be used. In one embodiment, a CCD sensor array 52 can be used to detect the reflected light beam 53b, which can allow a determination of the membrane deformation in high transversal resolution, and thus can allow the measurement of the pressure difference with increased precision. Such an embodiment can deliver more detailed information on the pressure and thus can be advantageous in the case where a control unit uses the pressure values to calculate and/or monitor the current flow of liquid and the administered dose of liquid medication.

The use of a CCD sensor array can have the further advantage that deviations within a certain range of the angular orientation of the array in regard to the micro-fluidic chamber 1 can be taken into account by a calibration measurement. This can increase the precision of the measurements and can allow to correct variations of the alignment of the reusable optical detection system 5 when coupled to a new sensor chamber.

The point of reflection 531 of the light beam 53a may be chosen on any position of the cover membrane 12. The closer the position 531 to the center of the membrane, the larger the deflection of the membrane 12 in the vertical direction can be (perpendicular to the undeflected membrane), which can correspond to a larger transversal shift of the reflection point 531' and thus of the reflected light beam 53b'. The closer the position 531 to the border of the micro-fluidic chamber 1, the larger the change of inclination of the membrane surface 12 and thus of the reflection angle upon deformation can be, which also can correspond to a larger shift of the reflected light beam 53b. To obtain maximum resolution, an optimum can be chosen from the position and orientation of the light emitting device 51 and photo sensors 52, 52'. A good position can be, for example, a reflection point at about 50% of the radius of the micro-fluidic chamber 1.

Figure 3:
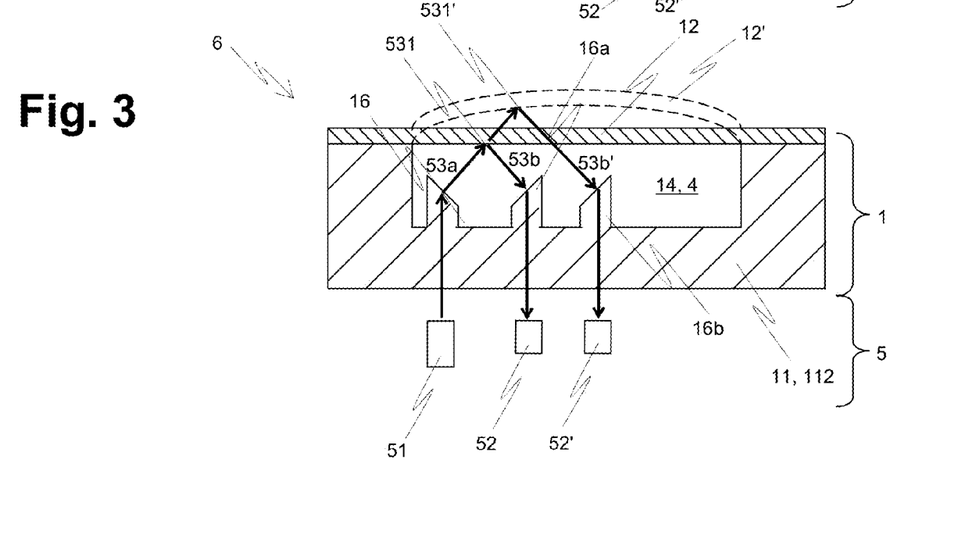
FIG. 3 illustrates another embodiment of a sensor in a cross-sectional view according to an embodiment of the present disclosure.

Another embodiment of a sensor is shown in FIG. 3. In this particular embodiment, the bottom structure 11 can have prism-like structures 16, 16a, 16b protruding from the bottom structure 11. A first prism-like structure 16 can be used to couple a collimated light beam 53a emitted by light emitting device 51 from the medium 112 of the bottom structure 11 into the liquid medium 4 in the micro-fluidic chamber 1, allowing for steeper incident angles of the light beam 53a on the cover membrane 12.

Two other prism-like structures 16a, 16b can be used to couple the reflected light beam 53b, 53b' back into the bottom structure medium material 112. Instead of two prism-like structures and two photo sensors 52, 52', as shown in FIG. 3, any multitude of such prisms and/or a multitude of photo sensors including a CCD sensor array can be applied to increase resolution.

One advantage of such an embodiment of a sensor can be the insensitivity of the optical detection system 5 to small deviations of its orientation in regard to the micro-fluidic chamber 1. Such small variations may result when a reusable part and a disposable part are coupled, even when guiding structures are provided.

Since the reflected light beams 53b, 53b' can be guided by the prism structures 16a, 16b to the corresponding optical sensors 52, 52' placed beneath the prism structures 16a, 16b, small lateral displacements of the sensors may not affect the accuracy of the optical detection system 5. Even larger displacements, affecting the alignment of the prism and the sensor 6 and thus the amount of light detected by the sensor 6, can be corrected since all sensors can be subject to the same amount of misalignment. Since all detectors are oriented in the same direction, the assembly of the device can be carried out by standard automatic placement machine, which can considerably reduce manufacturing costs.

Figure 4:
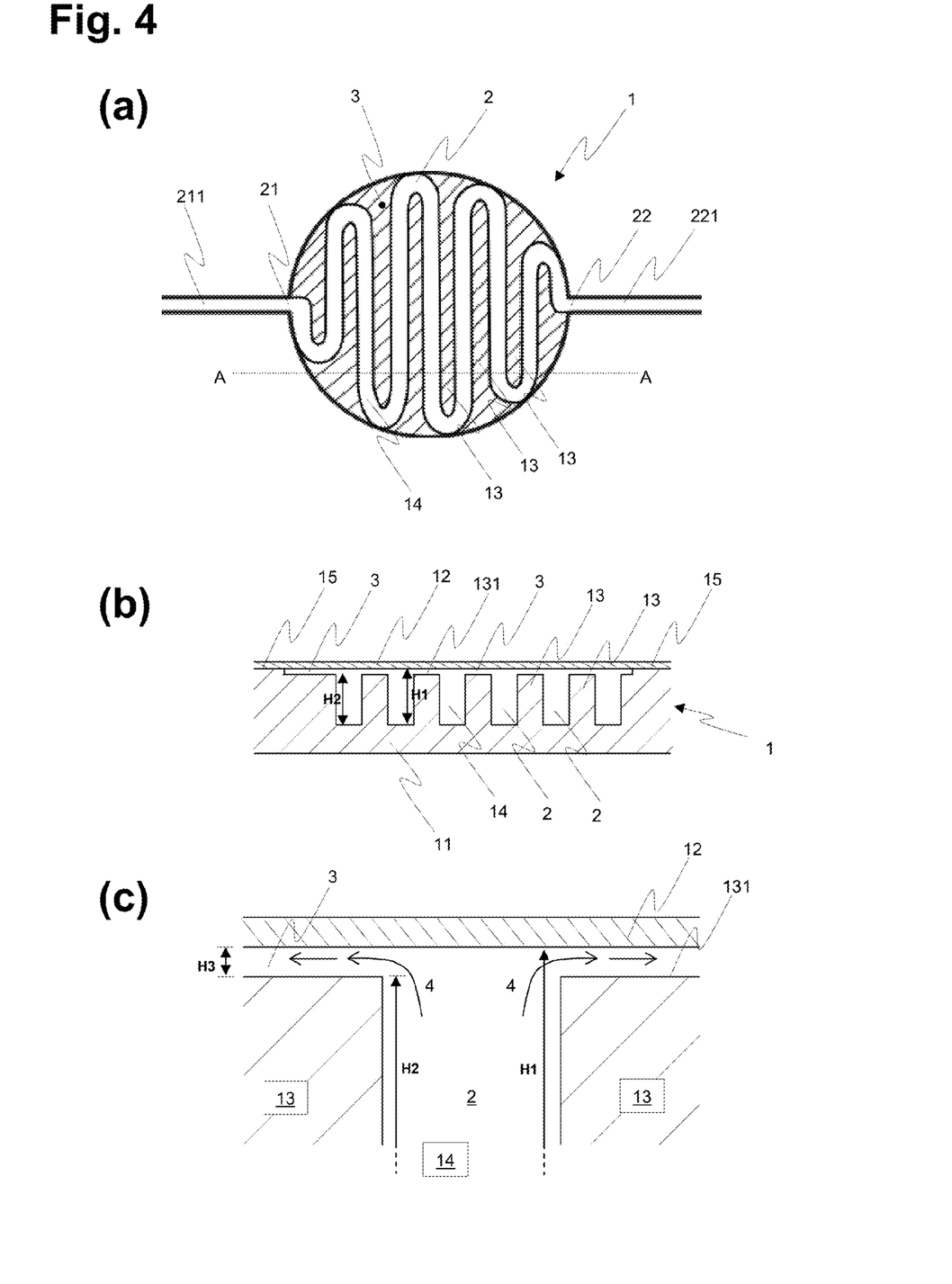
FIG. 4a illustrates an embodiment of a micro-fluidic chamber for use in a sensor in a top view according to an embodiment of the present disclosure.
FIG. 4b illustrates an embodiment of a micro-fluidic chamber for use in a sensor in a cross-section along plane A-A according to an embodiment of the present disclosure.
FIG. 4c illustrates a detail view of FIG. 4b according to an embodiment of the present disclosure.

One advantageous embodiment of a micro-fluidic chamber 1 that can be suitable for use in a sensor 6 is shown in FIG. 4. The circularly shaped fluid chamber 1 can comprise a bottom structure 11 and a top cover 12. The top cover 12 can be spaced from the bottom structure 11 by a certain height H1, thus defining an inner volume 14 of the micro-fluidic chamber 1. Eight walls 13 can be arranged in the fluid chamber 1 and define a meander-like fluid channel 2 that can run from an inlet 21 to an outlet 22 located on the opposite side of the micro-fluidic chamber 1. Thus the inlet conduit 211 and the outlet conduit 221 can be fluidly connected by the fluid channel 12.

The height H2 of the walls 13 can be less that the overall height H1 of the micro-fluidic chamber 1. As a result, there can be a fluid gap 3 between the top cover 12 and the upper surface 131 of the walls 13, with a height H3=H1−H2. The dimensions of the micro-fluidic chamber 1 and the walls 13, particularly the heights H1, H2, H3 can be chosen such that there are non-negligible capillary forces acting on a fluid 4 present in the micro-fluidic chamber 1. Fluid 4 in the fluid channel 2 can be dragged by the capillary forces into the fluid gap 3.

The specific dimensions can depend, on one hand, on the liquid used, and, on the other hand, on the properties of the surfaces of the top cover 12 and the top 131 of the walls 13, since this can eventually define the interface tensions between liquid, surfaces, and gas/air in the micro-fluidic chamber 1, which then will define the effective capillary forces for a certain geometric setting of a micro-fluidic chamber 1. Since in most cases, liquid medications can be aqueous solutions, it can be preferable that at least the most relevant surfaces, namely the surface of the top surface 131 of the wall 13 and the surface of the top cover 12 facing toward surface 131, be hydrophilic with a contact angle of <90°, in order to increase the overall capillary effect. For aqueous solutions, in one embodiment, a range for the height H3 of the gap 3 can lie between about 20 and about 200 µm. In another embodiment, a range for the height H3 of the gap 3 can lie between about 50 and about 150 µm.

The dimensions of the chamber 1 and the fluid channel 2 can be less critical. A typical diameter of a micro-fluidic chamber 1 may for example lie between about 2 to about 10 mm. The fluid channels may have a width of for example about 0.1 to about 1 mm, while the height H2 of the walls 13 in one embodiment, can lie in a range between about 0.25 to about 5 mm. In another embodiment, the height H2 of the walls 13 can lie in a range between about 0.5 and about 1 mm. The aspect ratio between the width of the fluid channel 2 and the height H2 can lie between about 0.25 and about 5, and, in one exemplary embodiment, can be about 1.

When a micro-fluidic chamber 1 is filled through inlet 21 with a liquid 4, the liquid can flow essentially along the fluid channel 2. The capillary forces can drag liquid 4 in the fluid channel 2 into the adjacent sections of the gap 3, effectively supplanting air present in the gap 3. It can be energetically more favorable for air to form spherical bubbles with minimum surface toward the hydrophilic surroundings, and thus no air bubbles remaining in the gap 3.

Figure 5:
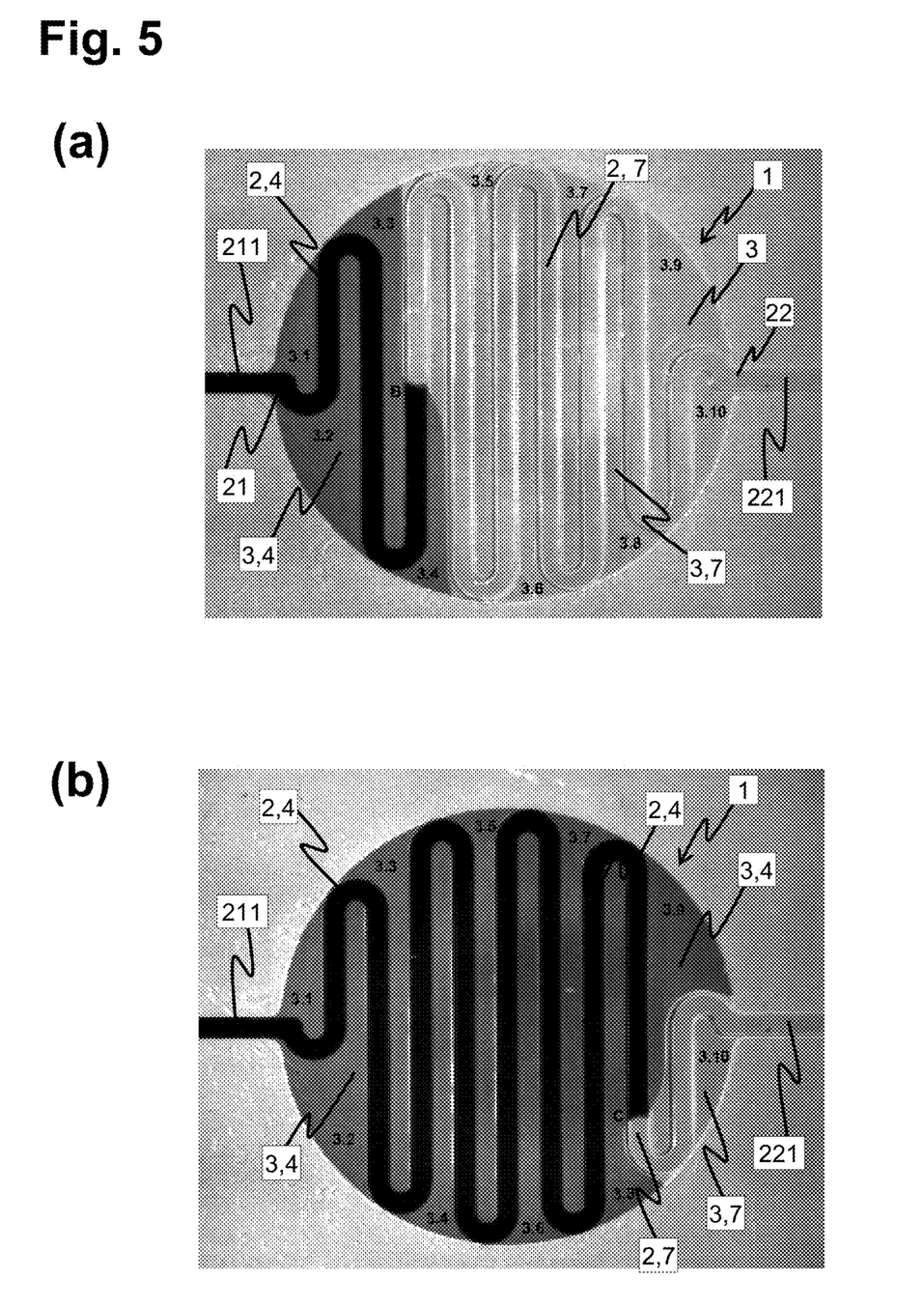
FIG. 5 illustrates the distribution of liquid in an embodiment of a micro-fluidic chamber for use in a sensor during the filling of the chamber in a real experiment, in two subsequent stages according to an embodiment of the present disclosure.

The first filling of such a micro-fluidic chamber 1 suitable for use with a sensor is experimentally demonstrated in FIG. 5. In FIG. 5(a), an aqueous liquid 4 has flown downstream through inlet conduit 211 and inlet 21 into the fluid channel 2, and can currently be at a position B. Due to the capillary forces in the gap 3, the liquid 4 can flow into the sections 3.1, 3.2, 3.3, 3.4 of gap 3 adjacent to the fluid channel 2 already filled. In the gap, the surrounding sections of the fluid channel 2 downstream of position B that are still filled with air or gas 7 can limit the further flow of the liquid. Thus the gap 3 can be filled section by section. FIG. 5(b) shows a later stage, where the liquid 4 has proceeded in the fluid channel 2 to a position C. All sections of the gap 3 can be filled with liquid 4, except section 3.10, which has not yet come into contact with the liquid and can still be filled with air 7. It is clearly visible in FIG. 5 that no air 7 can remain in the part of the chamber that has already been filled by liquid 4. When finally the liquid reaches the outlet 22 and the outlet conduit 221, the micro-fluidic chamber 1 can be filled completely. No air 7 can remain in the micro-fluidic chamber 1.

Air bubbles in the gap can be energetically less preferred than air bubbles in the fluid channel 2. As a consequence, no air bubbles can form in the gap 3 at a later stage, and if they do they can migrate into the fluid channel 2. Air bubbles in the fluid channel 2, on the other hand, cannot enter the gap 3 for energy reasons, but can be transported away by the liquid stream.

The shown capabilities of a micro-fluidic chamber 1 can be independent from its orientation in space. Since the capillary forces and interface tensions responsible for the smooth filling of the gap can be much stronger than the gravitational force acting on the liquid, and the buoyancy force acting on the air bubbles in the liquid, the micro-fluidic chamber finally can be completely filled with liquid 4 independent on its orientation. Thus the filling behavior of such a micro-fluidic chamber 1 can be predictable and reproducible, which can be advantageous for use in a sensor.

Since the operational internal volume of a micro-fluidic chamber 1 can be smaller than that of a hollow micro-fluidic chamber 1 with similar dimensions, the dead volume—the portion of the fluid volume in a fluid system that can never be drained and eventually can be lost when the sensor is discarded—can considerably be reduced.

A further advantage of the disclosed micro-fluidic chamber 1 can be the fact that an air bubble that enters the chamber through the inlet can be guided through the fluid channel to the outlet. Since the effective cross-sectional area of the fluid channel can essentially be constant over its length, the liquid flow can also be constant over its length, and does not drop at certain positions. Thus, bubbles cannot be caught in the fluid chamber.

Figure 6:
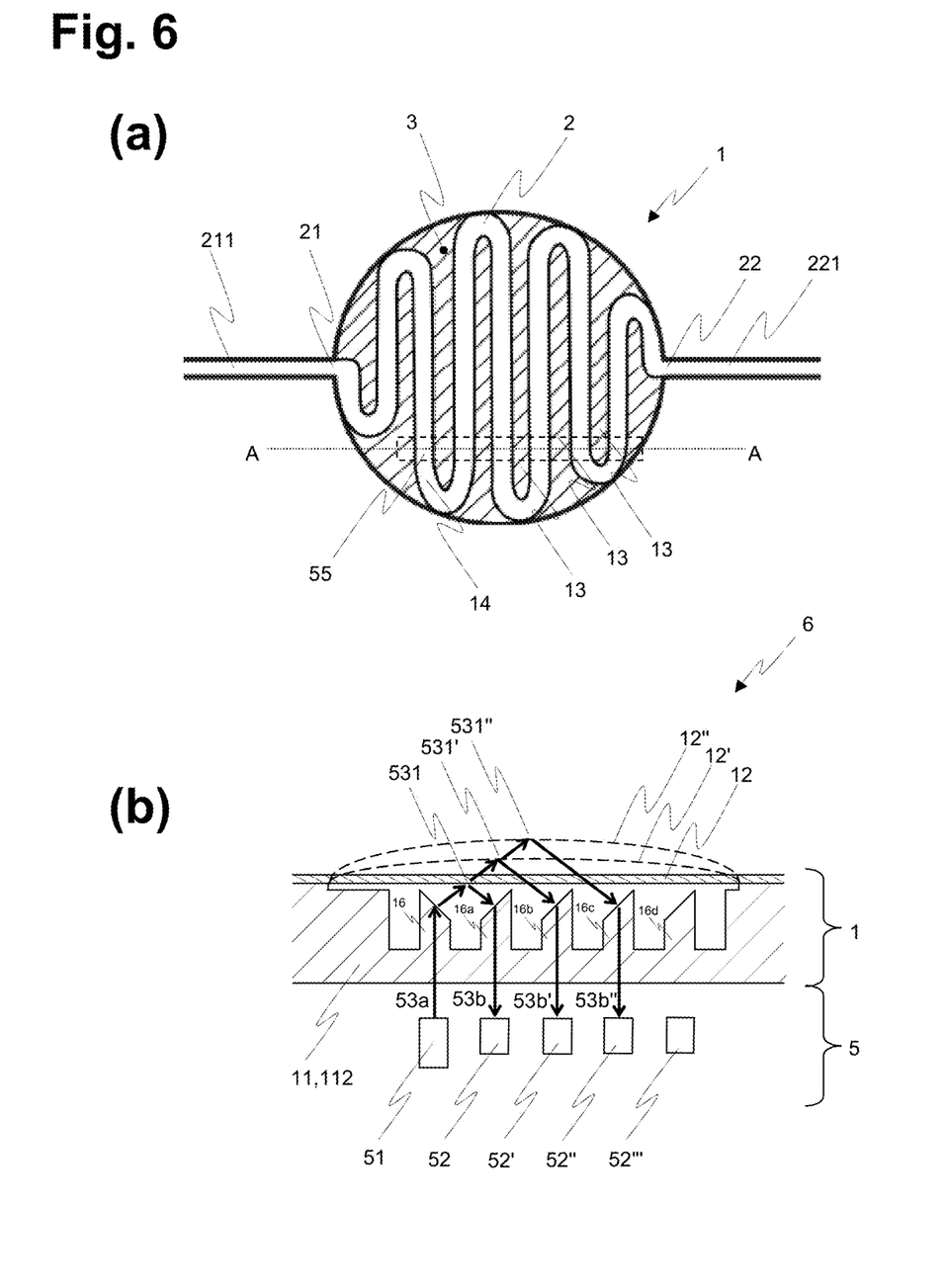
FIG. 6a illustrates an embodiment of a sensor with prism-like structures in combination with a meandering fluid path in a top view according to an embodiment of the present disclosure.
FIG. 6b illustrates an embodiment of a sensor with prism-like structures in combination with a meandering fluid path in a cross-section along line A-A according to an embodiment of the present disclosure.

An exemplary sensor 6 is disclosed in FIG. 6 and can exemplify a useful embodiment of a sensor, where an optical detection scheme of a senor can be combined with the advantages of a micro-fluidic chamber 1 with meandering fluid channel 2. The micro-fluidic chamber 1 of such a sensor can essentially correspond to the embodiment shown in FIG. 4, while detection can be similar to FIG. 3.

In a rectangular detection area 55, the walls 13 of the micro-fluidic chamber 1 can be reduced to prism-like structures 16, 16a, 16b, in order to couple an incident light beam 53a propagating in the wall into the liquid 4, and to couple the reflected light beam 53b, 53b' back into the walls and the bottom structure 11. The prism structures can form only a narrow gap in the walls 13. This can prevent that the fluidic resistance along the detection area falls below the flow resistance along the fluidic channel 2.

A light-emitting device 51 can be arranged directly below the first prism-like structure 16, and can emit a collimated light beam 53a that can propagate in the wall until it reaches the inclined prism surface, where it can be refracted toward the reflection point 531. After reflection on the cover membrane 12, the reflected light beam 53b can impinge on the prism surface of a second prism-like structure 16a, where it can be refracted toward a photo sensor 52 arranged directly below the prism 16a.

When the pressure difference increases, the cover membrane 12 can deformed, and the reflection point 531' can move to the right. The reflected light beam 53b can now impinge on the prism surface of the third prism-like structure 16b, and can reach a second photo sensor 52'. With further increasing pressure difference, the reflected light beam can reach next prism 16c, and so on.

The inclination angle and the general dimensions of the prismatic structures can depend on the dimensions and properties of the micro-fluidic chamber 1, on the wave-length used for the light beam, the refraction indices of the bottom structure material and the liquid medium, and other factors, and can be adopted for a particular sensor geometry.

Figure 7:
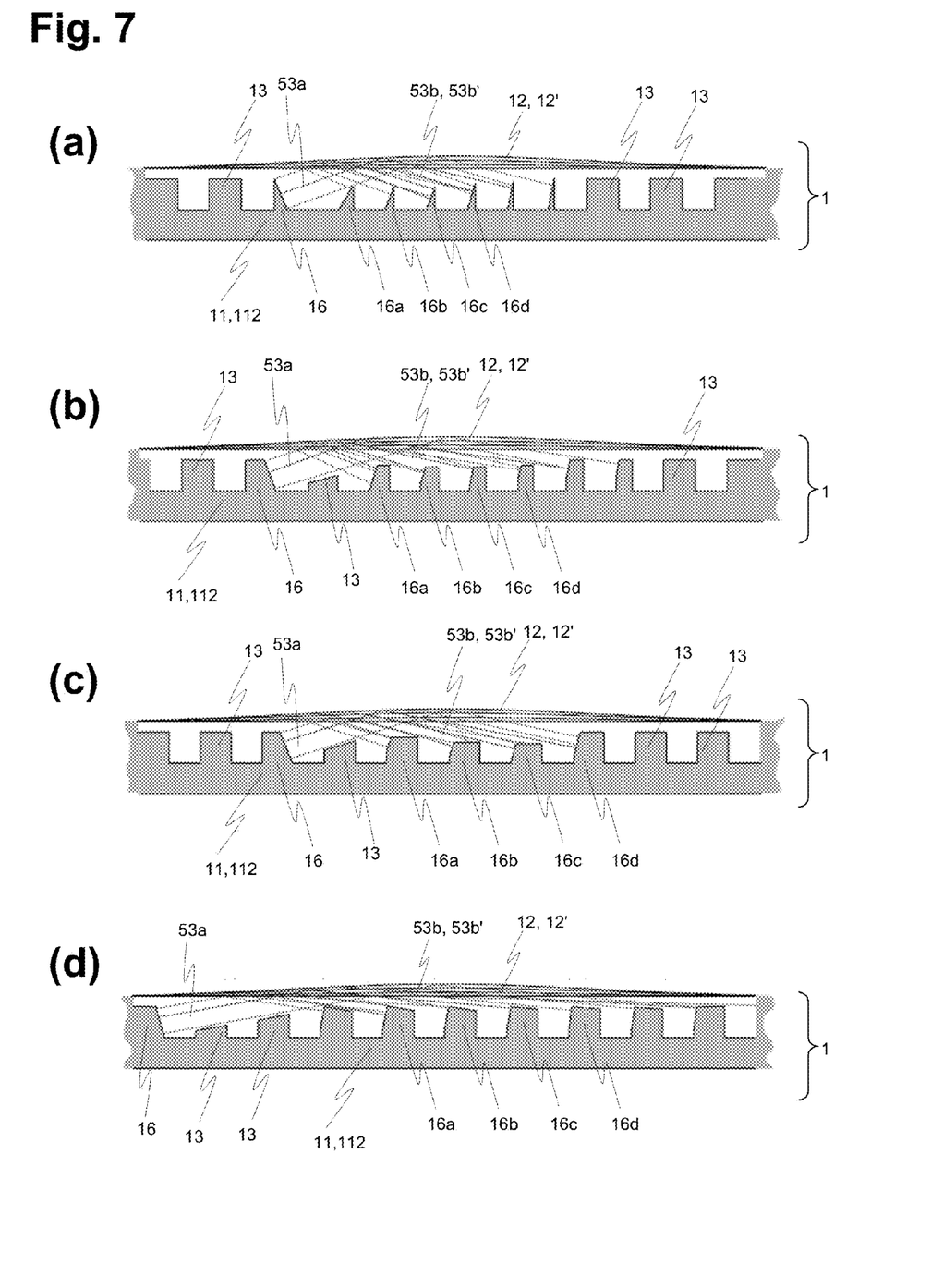
FIG. 7 illustrates different alternative variants of prism-structures for use in a sensor as shown in FIG. 6 according to an embodiment of the present disclosure.

Further examples of possible prism structures are depicted in FIGS. 7(a) to (d). In FIGS. 7(a) and (b), the prism structures can be narrow, with large prism surfaces for collecting the impinging light. Such a design can be advantageous from the point of view of optical detection. However, the narrow prism-structures can lead to a decrease of the flow resistance along the detection area 55, which can be less advantageous for the micro-fluidic chamber 1.

In FIGS. 7(c) and (d), the prism-like structures can be as broad as the other walls 13. This can increase the flow resistance along the detection area. On the other hand, the surface of the prism that is available for receiving light can be decreased.

Figure 8:
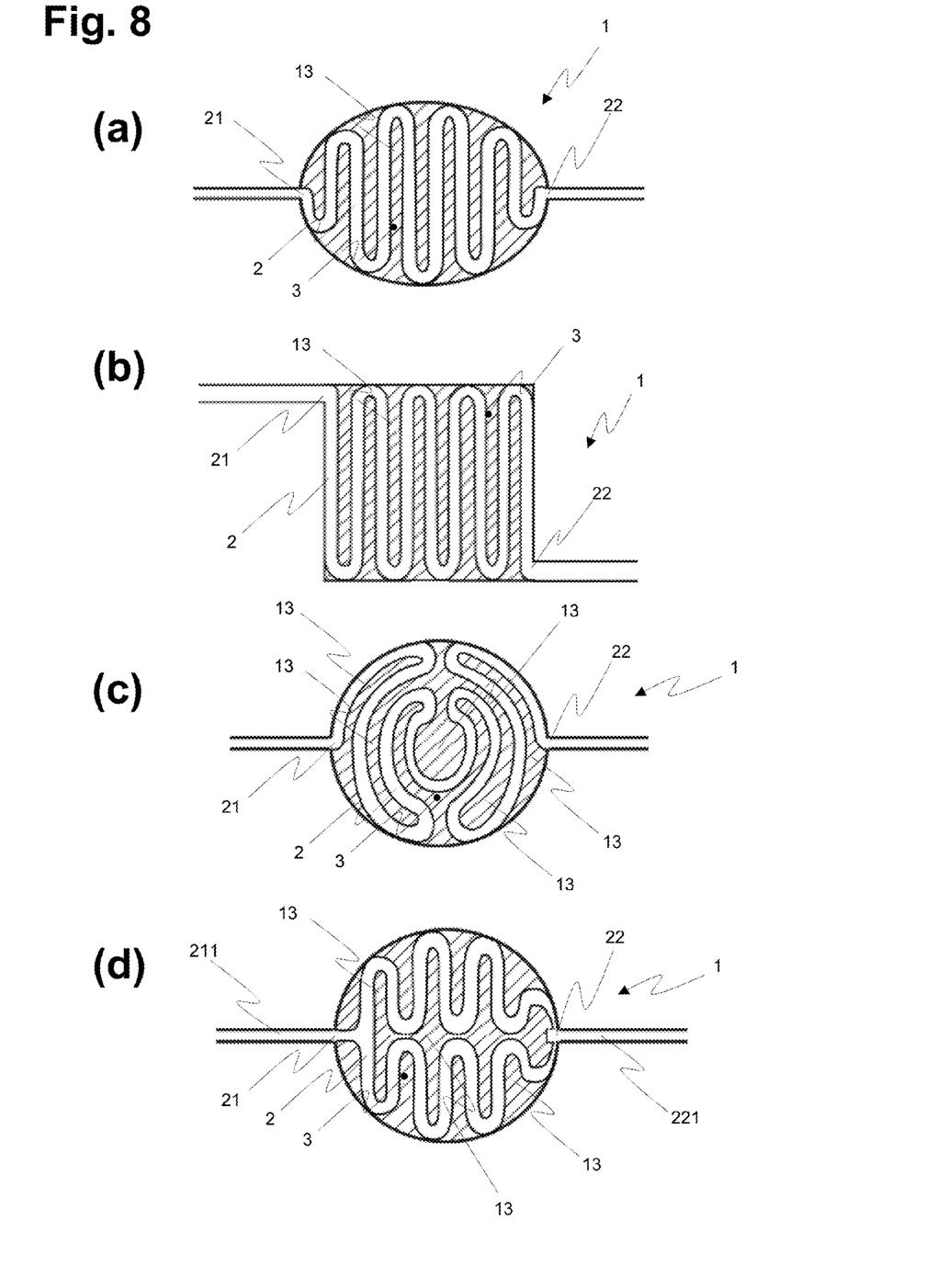
FIG. 8 illustrates four exemplary embodiments of micro-fluidic chambers for use in a sensor according to an embodiment of the present disclosure.

A micro-fluidic chamber 1 may have circular shape, as shown in FIG. 6, or may have any other suitable shape. The same can hold true for the specific design of the fluid channel 2 in the micro-fluidic chamber 1. Depending on the design of a sensor 6, some embodiments of micro-fluidic chambers 1 may be preferable over others. FIG. 8 shows a number of possible variants of micro-fluidic chambers 1 suitable for use with a sensor. In FIG. 8(a), the meanders of the fluid channel 2 can be an elliptically shaped chamber 1, while in the embodiment of FIG. 8(b), the micro-fluidic chamber 1 can have a rectangular shape. In FIG. 8(c), a circularly shaped chamber 1 with an alternative course of a meandering fluid channel 12 is shown.

Instead of having only one fluid channel 2, the walls 13 of the micro-fluidic chamber 1 may define two or more fluid channels within the micro-fluidic chamber 1, extending from a common inlet to a common outlet. FIG. 8(d) shows such an embodiment of a micro-fluidic chamber 1. An inlet conduit 211 can open toward the chamber 1 through a common inlet 21. The fluid channel can then split into two separate fluid channels 2, 2', which can join again at a common outlet 22. In such an embodiment, flow barriers can be provided that ensure that during the filling procedure the micro-fluidic chamber 1 is completely filled before the liquid flow can proceed further through the outlet 22.

A curved or meandering design of the fluid channel 2 can be advantageous for fluid chambers with larger base areas, since the longest possible distance between the fluid channel 2 and an outer edge of the gap 3 can be short. In addition, the meandering fluid channel 2 can be used as an efficient means to limit the maximum flow through a fluidic system.

In sensors discussed so far, the micro-fluidic chamber 1 can comprise a bottom structure 11 and a top cover membrane 12, which can be sealed together in a sealing area 15 along an outer rim of the micro-fluidic chamber 1. Suitable materials of the bottom substrate 11 and the top cover 12 can be, for example, polymer materials. Suitable methods for connecting the two substrates 11, 12 can be, for example, thermal bonding, laser bonding, gluing and the like.

The walls 13 can be an integral part of the bottom substrate 11. In such a case, the fluid channel 2, and even the inlet and outlet conduits, can, as an example, be produced by embossing the necessary void structures into a flat bottom structure 12. To obtain the necessary gap 3, a thin spacer layer with height H3 can be arranged between bottom layer structure 11 and top layer 12 around the micro-fluidic chamber 1, or may produce the gap 3 together with the fluid channel 2 and the walls 13 in the embossing step. Another suitable technology for the manufacture of micro-fluidic chambers can be injection molding.

In a possible alternative approach, the walls 13 can be separate filling structures, mounted onto a flat bottom layer 11. In that approach, a filling body may be attached to a bottom layer 11, and then may be arranged between the bottom layer 11 and an adjacent top layer in a sandwich-like manner.

In one embodiment of a sensor 6, the wave length used for detection can be chosen such that it can have a high absorption coefficient in the liquid, which in most cases can be an aqueous solution. Useful wavelengths can include those wavelengths where water has a high absorption coefficient, for example, about 630 nm or about 1400 nm. An absorption maximum for a typical insulin formulation can be given at about 270 nm. Thus such a wavelength can be particularly advantageous for use with insulin pump systems. Although a part of the irradiated light can be absorbed in the liquid medium 4, the photo sensors can receive sufficient signal to deliver reliable results.

If, however, an air bubble is dragged along the fluid channel 2, and reaches the detection area 55, the absorption can be strongly reduced, and the signal received by one or more of the photo sensors can increase significantly. This sudden increase in signal intensity can be subsequently used to generate a warning message for the user and/or the control system of an infusion pump that an air bubble is present in the fluidic system, and that the reliability of the sensor 6 may be compromised. Thus, a sensor 6 can also be used to detect air bubbles in a fluidic system, and to determine if its pressure measurement values may be erroneous due to the presence of an air bubble in the sensor.

Figure 9:
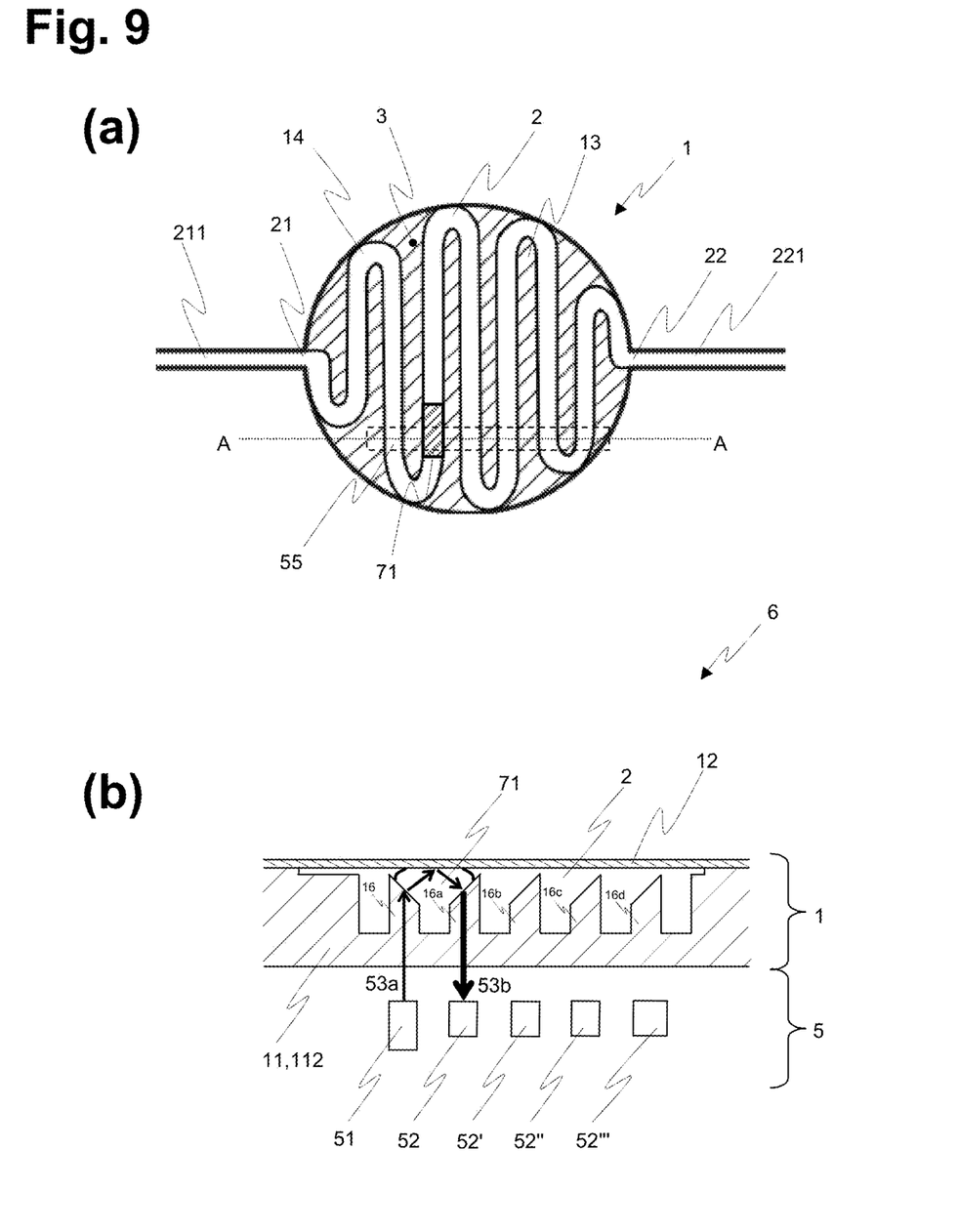
FIG. 9 illustrates the sensor according to FIG. 6, with an air bubble present in the fluid channel according to an embodiment of the present disclosure.

FIG. 9 shows a sensor 6 as shown in FIG. 6 being used as an air bubble sensor. An air bubble 71 in the liquid stream has entered the micro-fluidic chamber 1. For energetic reasons it cannot enter the fluid gap 3, and is dragged along the fluid channel 2. When the air bubble 71 reaches the detection area 55, the incident light beam 53a and the reflected light beam 53b can pass through the air bubble, as shown in FIG. 9(b).

The light intensity detected by the detector 52 can increase which the sensor 6 can interpret as the detection of an air bubble.

Taking into account the known geometry of the micro-fluidic chamber 1, the current conveying velocity of the liquid and the time period between the increase of the light intensity (corresponding to the front of the air bubble) and the decrease of the light intensity back to a normal value (marking the end of the air bubble), such a sensor 6 can even be able to determine the volume of the passed air bubble. Such information may then be used by a controlling unit to assess the situation and to take the necessary steps.

In an embodiment of a sensor 6 directed to the use as a air bubble sensor, the membrane 12 may be realized as a semi-rigid membrane, or even as a rigid cover.

Figure 10:
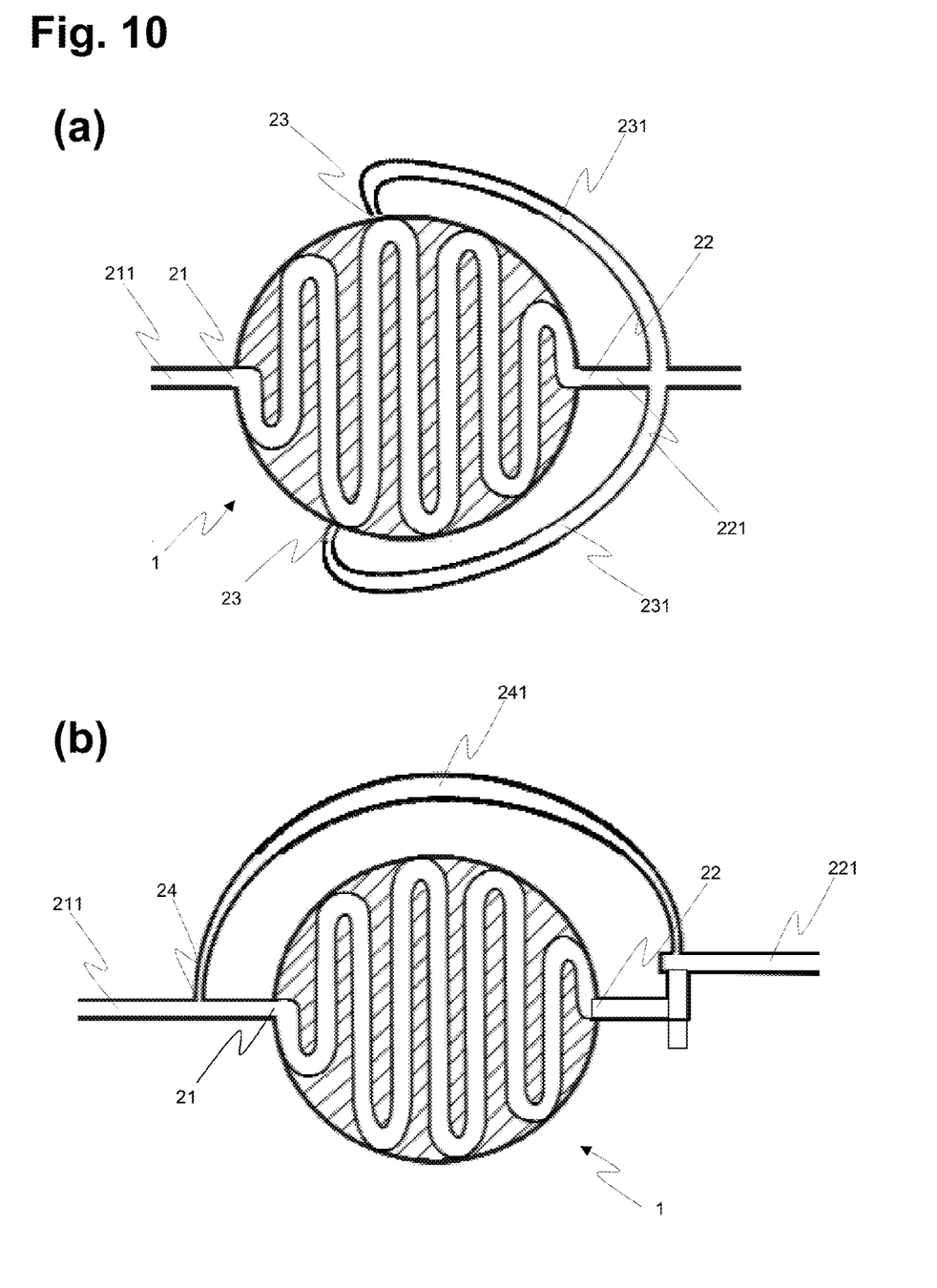
FIG. 10a illustrates an embodiment of a micro-fluidic chamber for use in a sensor with additional outlets along the fluidic channel in the chamber, providing bubble-trap capabilities according to an embodiment of the present disclosure.
FIG. 10b illustrates an embodiment of a micro-fluidic chamber for use in a sensor with a bypassing additional conduit according to an embodiment of the present disclosure.

Two further embodiments of micro-fluidic chambers 1 for use with a sensor device 6 are disclosed in FIG. 10. In FIG. 10(a), two additional outlet openings 23 can be located at different positions along the meandering fluid channel 2, from which additional outlet conduits 231 branch off. Downstream of the main outlet 22, the outlet conduits 221, 231 can converge again to a common outlet conduit. The additional outlet openings 23 can be smaller than the main outlet opening 22. The width of the narrow outlets 23 can be about 50% or less of the width of the fluid channel 2. For an air bubble with certain dimensions, it can be energetically less favorable to enter the narrow outlet 23, due to the interface tensions, than to stay in the comparably wide fluid channel 2. Thus the bubbles can stay inside of the fluid channel, where they can be eventually detected by the optical detection system 5. Since three outlets 23, 22 can be available, the through-put of liquid through the sensor 6 can be increased.

FIG. 10(b) depicts another embodiment of a sensor with an additional conduit 241 bypassing the micro-fluidic chamber 1. The bypass conduit 241 can directly connect the inlet conduit 221 to the outlet conduit 221. The width of the inlet 24 of the bypass conduit 241 can be much smaller, about 50% or less, than the width of the inlet conduit 211. It thus cannot be favorable for an air bubble to enter the inlet 24 and bypass conduit 241, and the air bubble can enter the sensor 6, where it can detected. To ensure that both the bypass conduit 241 and the micro-fluidic chamber 1 can completely be filled during the first filling procedure, a flow barrier can be used, as already discussed previously.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

I claim:

1. A sensor for use in a liquid medication delivery system, the sensor comprising:
   a micro-fluidic chamber comprising a rigid bottom substrate and a cover, the bottom substrate and the cover defining an inner volume of the chamber, the chamber being connected to a fluidic system through which a liquid medication can be delivered; and
   an optical detection system that is configured to emit one or more light beams toward the cover and to observe the one or more light beams reflected from the cover, wherein the cover is a flexible, resilient cover membrane, and the optical detection system is configured to determine a deformation of the cover membrane, and wherein the optical detection system is arranged on a side of the bottom substrate opposite to the cover.

2. The sensor according to claim 1, wherein the one or more light beams impinging on the cover, the one or more reflected light beams pass through the bottom structure or combinations thereof.

3. The sensor according to claim 1, wherein wavelength of the emitted light beams is chosen such that a liquid in the micro-fluidic chamber shows a high absorption coefficient at that wavelength.

4. A sensor according to claim 1, wherein the optical detection system comprises two or more photo sensors.

5. A sensor according to claim 1, wherein the optical detection system comprises a photo sensor array.

6. A sensor according to claim 1, wherein the one or more light beams are reflected on a fluid-contacting surface of the cover.

7. A sensor according to claim 1, wherein the sensor is a pressure sensor, an air bubble sensor or combinations thereof.

8. The sensor according to claim 1, wherein the bottom substrate comprises prism-like structures for coupling a light beam from a bottom structure material into a liquid in an inner volume of the micro-fluidic chamber, from the liquid into the bottom structure material or from combinations thereof.

9. The sensor according to claim 1, further comprising,
   one or more walls positioned in the micro-fluidic chamber, the walls defining a fluid channel therebetween such that the fluid channel extends from an inlet of the micro-fluidic chamber to an outlet of the micro-fluidic chamber; wherein each of the walls has a height (H2) less than a height (H1) of the micro-fluidic chamber defined by the distance between the bottom substrate and the cover, so as to define a fluid gap between a top surface of each wall and the cover, and wherein the dimensions (H1, H2) of the walls and the micro-fluidic chamber are chosen such that the fluid gap will be filled with liquid by capillary forces via the fluid channel when liquid is introduced into the micro-fluidic chamber.

10. A sensor according to claim 9, wherein prism-like structures are provided in the walls for coupling a light beam from a bottom structure material of the wall into a liquid in an inner volume of the micro-fluidic chamber, from the liquid into the bottom structure material, or from combinations thereof.

11. A sensor according to claim 9, wherein the fluid channel has a curved shape.

12. A sensor according to claim 9, further comprising,
   an additional conduit bypassing the micro-fluidic chamber and fluidly connecting an inlet conduit and an outlet conduit of the micro-fluidic chamber.

13. An infusion pump for use in a liquid medication delivery system comprising a sensor according to claim 1.

14. A liquid medication delivery system comprising a sensor according to claim 1.

15. The use of a sensor according to claim 1 for measuring the pressure in a fluidic system, for measuring the presence of air bubbles in a fluidic system, or for combinations thereof.

\* \* \* \* \*